United States Patent [19]

Bregeault et al.

[11] Patent Number: 4,983,767
[45] Date of Patent: Jan. 8, 1991

[54] PREPARATION OF ALIPHATIC CARBOXYLIC ACIDS BY OXIDATION OF MONOCYCLIC KETONES

[75] Inventors: Jean-Marie Bregeault, Boussy Saint-Antoine; Bassam El-Ali, Paris Cedex; Jacques Martin, Orsay, all of France

[73] Assignee: Rhone-Poulenc Chimie, Courbevoie, France

[21] Appl. No.: 393,803

[22] Filed: Aug. 15, 1989

[30] Foreign Application Priority Data

Aug. 16, 1988 [FR] France ................. 88 11075

[51] Int. Cl.$^5$ .......................... C07C 51/245
[52] U.S. Cl. ..................... 562/528; 502/152; 502/209; 502/312; 562/590
[58] Field of Search ............ 562/528, 590; 502/152, 502/209, 312

[56] References Cited

U.S. PATENT DOCUMENTS 4,510,321  4/1985  Masilamani et al. ............ 562/421
4,739,114  4/1988  Lee et al. ....................... 562/524
4,883,910  11/1989  Seidel ........................... 562/528

*Primary Examiner*—Werren B. Lone
*Assistant Examiner*—Vera C. Clarke
*Attorney, Agent, or Firm*—Burns, Doane, Swecker & Mathis

[57] ABSTRACT

Aliphatic carboxylic acids, e.g., adipic acid, are prepared by oxidizing a monocyclic ketone with molecular oxygen or an oxygen-containing gas, in the presence of a catalytically effective amount of a vanadium compound having one of following formulae (I) and (II):

$$H_{3+n}[PM_{12-n}V_nO_{40}] \cdot y\ H_2O \qquad (I)$$

$$VO(Y)_m \qquad (II)$$

in which n is an integer greater than or equal to 1 and less than or equal to 6; M is a molybdenum or tungsten atom; y is an integer ranging from zero to less than 50; Y is an acetylacetonate group or an alkoxy radical containing from 1 to 10 atoms; and m is 2 or 3.

15 Claims, No Drawings

PREPARATION OF ALIPHATIC CARBOXYLIC ACIDS BY OXIDATION OF MONOCYCLIC KETONES

BACKGROUND OF THE INVENTION

1. Field of the Invention

The present invention relates to the preparation of aliphatic carboxylic acids by the oxidation of cyclic ketones by means of molecular oxygen or an oxygen-containing gas.

SUMMARY OF THE INVENTION

Briefly, the present invention features a process for the preparation of aliphatic carboxylic acids by oxidizing monocyclic ketones with molecular oxygen or a gas comprised thereof, in the presence of a catalytically effective amount of a vanadium compound having one of the following formulae (I) or (II):

$$H_{3+n}[PM_{12-n}V_nO_{40}] \cdot yH_2O \quad (I)$$

$$VO(Y)_m \quad (II)$$

in which n is an integer greater than or equal to 1 and less than or equal to 6; M is a molybdenum or tungsten atom; y is an integer, less than 50, which may be zero; Y is an acetylacetonate group or an alkoxy group containing from 1 to 10 atoms; and m has a value of 2 or 3.

DETAILED DESCRIPTION OF THE PREFERRED EMBODIMENTS OF THE INVENTION

More particularly according to the present invention, by the term "monocyclic ketones" are intended compounds, the carbonyl group of which is directly bonded to carbon atoms to form a single saturated ring having from 5 to 8 carbon atoms, with the proviso that the ring may additionally contain one or two substituents selected from among $C_1$–$C_4$ alkyl radicals and the phenyl radical.

Exemplary of such ketones, the following are representative:

Cyclopentanone;
Cyclohexanone;
2-Methylcyclohexanone;
2-Methylcyclopentanone;
2,5-Dimethylcyclopentanone;
2,6-Dimethylcyclohexanone; and
2-Phenylcyclohexanone.

By "aliphatic carboxylic acids" are intended the ketoacids and diacids. These acids may be at least partially converted, in situ in the presence of an alcohol or an ether, to be corresponding esters or diesters, as soon as they are formed. The preparation of these partially or totally esterified forms of the acids: under consideration is also within the scope of the present invention.

Cyclohexanone is a particularly preferred starting material, since it results in the formation of adipic acid.

The process according to the present invention requires the presence of a catalyst selected from among the vanadium compounds corresponding to either one of the formulae (I) and (II) given above.

Exemplary of vanadium compounds corresponding to formula (I), the following are representative:
$H_4[PW_{11}V_1O_{40}] \cdot 30H_2O$
$H_4[PMo_{11}V_1O_{40}] \cdot 33H_2O$
$H_5[PMo_{10}V_2O_{40}] \cdot 30\text{-}36H_2O$
$H_6[PMo_9V_3O_{40}] \cdot 34H_2O$.

Exemplary of vanadium compounds corresponding to formula (II), the following are representative:
Vanadyl bis(acetylacetonate); and
Isopropyl vanadate.

In a preferred embodiment of the invention, vanadium compounds corresponding to formula (I) above are used.

More specifically, compounds corresponding to formula (I) are preferably used, in which n has the value of 1 or 2; and y is greater than or equal to 30 and less than or equal to 40.

A preferred class of vanadium-based catalysts includes the compounds corresponding to formula (I) in which M is a molybdenum atom.

These compounds (molybdo- or tungstovanadophosphoric acids) as well as their methods of preparation are well known to this art. Compare also G. A. Tsigdinos and C. J. Hallada, *Inorganic Chemistry*, Vol. 7, pages 437 et seq. (March 1968); P. Courtin, *Rev. Chim. Min.*, 8, 75 (1971); and M. Canneri, *Gazz. Chim. Ital.*, 56, 871 (1926).

The amount of catalyst to be used may vary over wide limits. This amount, expressed as moles of vanadium per liter of reaction medium, generally ranges from 0.001 to 0.5 mol.l$^{-1}$. Preferably, this concentration ranges from 0.005 to 0.1 mol.l$^{-1}$.

The oxidation generally is carried out in a liquid medium, the liquid medium comprising the monocyclic ketone which is to be oxidized and, if necessary, a solvent or diluent which is inert under the reaction conditions with respect to the constituents of the reaction mixture.

Exemplary of such solvents or diluents are the halogenated or unhalogenated aromatic hydrocarbons, the nitrated hydrocarbons such as nitrobenzene and nitromethane, the nitriles such as acetonitrile, carboxylic acids such as acetic acid and water.

The oxidation may also be carried out in a liquid medium comprising an alcohol, and in particular a $C_1$–$C_4$ alkanol which is capable of reacting with the acid (or the diacid) produced to form the corresponding ester (or diester).

The reaction medium may, of course, contain a solvent mixture, and in particular a solvent mixture which is inert, as indicated above, and an alcohol.

The reaction medium may also contain an ether such as diglyme.

The initial concentration of the substrate to be oxidized may also vary over wide limits. In general, it ranges from 50 to 400 g.l$^{-1}$, and preferably from 150 to 250 g.l$^{-1}$.

The temperature at which the process according to the present invention is carried out normally ranges from 25° to 120° C., and preferably from 40° to 100° C.

The molecular oxygen used as the oxidizing agent in the present process may be in the form of pure oxygen, or of mixtures of oxygen and other inert gases. Thus, air or even oxygen/nitrogen mixtures richer or poorer in oxygen than air may be used.

The oxidation may be carried out under a stream of oxygen or of the gas containing oxygen, or by charging the reaction medium with a certain amount of oxygen. The partial pressure of oxygen may range from 0.2 bar to 20 bar, but in actual practice it is not necessary for the pressure to exceed 10 bar.

Upon completion of the reaction or at the end of the required reaction time, the products obtained may be recovered and separated by any appropriate method, for example by distillation.

In order to further illustrate the present invention and the advantages thereof, the following specific examples are given, it being understood that same are intended only as illustrative and in nowise limitative.

EXAMPLES 1 TO 5

These examples illustrate the oxidation of 2-methylcyclohexanone.

12.4 mmol 2-methylcyclohexanone, a catalyst (the nature and amount of which are indicated in the following Table I for Examples 1 to 5), and 6 cm³ acetonitrile were placed in a 20 ml glass tube, connected to a gas holder containing molecular oxygen.

After closing the tube, its temperature was increased to 60° C. under stirring for the time indicated in the Table.

After 4 hours (or 24 hours) at the reaction temperature, the mixture was cooled and analyzed by gas phase chromatography.

The particular conditions and the results obtained are also reported in Table I below, in which:

(i) S (OHA) indicates the selectivity for 6-oxoheptanoic acid, $$\left[\frac{\text{number of moles of product formed}}{\text{number of moles of substrate converted}} \times 100\right]$$

(ii) DC indicates the degree of conversion of the 2-methylcyclohexanone.

TABLE I

| Example | CATALYST TYPE | mol. l⁻¹ | Time (h) | DC (%) | S(OHA) (%) |
|---|---|---|---|---|---|
| 1 | VO(acac)₂ | 0.12 | 24 | 49 | 89.0 |
| 2 | VO[OCH(CH₃)₂]₃ | 0.02 | 24 | 57.5 | 89.5 |
| 3 | H₄[PW₁₁V₁O₄₀].30 H₂O | 0.02 | 4 | 57 | 89.5 |
| 4 | H₄[PMo₁₁V₁O₄₀].33 H₂O | 0.02 | 4 | 93.5 | 89.5 |
| 5 | H₅[PMo₁₀V₂O₄₀].30-36 H₂O | 0.01 | 4 | 98 | 89.0 |

EXAMPLE 6

This example illustrates the oxidation of cyclohexanone.

The procedure of Example 5 was repeated, except that the 2-methylcyclohexanone was replaced with the same molar amount of cyclohexanone.

All of the other reaction conditions remained the same, and adipic acid was obtained with a selectivity of 75%, the degree of conversion of the cyclohexanone being 85%.

EXAMPLE 7

The procedure of Example 5 was repeated, except that the acetonitrile was replaced with the same volume of nitromethane. All of the other reaction conditions remained the same, and the following results were obtained:

The degree of conversion of the 2-methylcyclohexanone:
(DC) was 98%.

The yield of 6-oxoheptanoic acid [YD (OHA)] was 81.5%, $$\left[\frac{\text{number of moles of product formed}}{\text{number of moles of initial substrate}} \times 100\right]$$

EXAMPLE 8

The procedure of Example 5 was repeated, except that the acetonitrile was replaced with the same volume of acetic acid.

In 6 hours of reaction, all other conditions remaining the same, the following results were obtained:
DC=81%
YD (OHA)=69%.

EXAMPLE 9

The procedure of Example 5 was repeated, except that the acetonitrile was replaced with the same volume of methanol.

In 6 hours of reaction, all other conditions remaining the same, the following results were obtained:
DC=54%.

The yield of 6-oxoheptanoic acid methyl ester was 49% [YD (EST)].

EXAMPLE 10

The procedure of Example 5 was repeated, except that the acetonitrile was replaced with the same volume of diglyme (CH₃—O—CH₂—CH₂—O—CH₃).

In 24 hours of reaction, all other conditions remaining the same, the following results were obtained:
DC=96%
YD (OHA)=74%
YD (EST)=16%.

EXAMPLE 11

The procedure of Example 5 was repeated, except that 1 cm³ acetonitrile was replaced with 1 cm³ methanol.

In 6 hours of reaction, all other conditions remaining the same, the following results were obtained:
DC=96%
YD (OHA)=4%
YD (EST)=86%.

EXAMPLES 12 TO 14

A series of experiments was carried out according to the procedure of Examples 1 to 5 above on a charge containing no solvent, but 12.4 mmol (1.5 cm³) 2-methylcyclohexanone and a catalyst, the nature and amount of which are given in Table II below, at 60° C. and under a partial oxygen pressure of one atmosphere. The particular reaction conditions and the results obtained are also reported in Table II below, in which the conventions used were the following:

(i) DC indicates the degree of conversion of the 2-methylcyclohexanone;

(ii) YD (OHA) indicates the yield of 6-oxoheptanoic acid, $$YD = \frac{\text{number of moles of product formed}}{\text{number of moles of initial substrate}} \times 100$$

TABLE II

| Example | CATALYST TYPE | mmol | Time (h) | DC (%) | DC(OHA) (%) |
|---------|---------------|------|----------|--------|-------------|
| 12 | $H_5[PMo_{10}V_2O_{40}]\cdot 30-36\ H_2O$ | 0.075 | 8 | 90 | 75 |
| 13 | $VO[OCH(CH_3)_2]_3$ | 0.375 | 24 | 50 | 40 |
| 14 | $[VO(acac)_2]$ | 0.90 | 24 | 49 | 41 |

EXAMPLE 15

An experiment was carried out employing the procedure described above on a charge containing:
(i) 4.85 mmol cyclohexanone;
(ii) 5 cm³ acetonitrile;
(iii) 1 cm³ methanol; and
(iv) 0.05 mmol $H_5[PMo_{10}V_2O_{40}]\cdot 30-36\ H_2O$.

The partial oxygen pressure was one atmosphere. In 24 hours of reaction at 60° C., the following results were obtained:
DC=98%
Yield of dimethyl adipate: 54%.

EXAMPLES 16 TO 20

A series of experiments utilizing various substrates was carried out according to the operating procedure described above, under the following common reaction conditions:

(a) $H_5[PMo_{10}V_2O_{40}]\cdot 30-36\ H_2O$ was used as the catalyst;
(b) the solvent was acetonitrile (6 cm³ except where otherwise indicated);
(c) the temperature was 60° C.; and
(d) the partial oxygen pressure was one atmosphere.

The particular reaction conditions and the results obtained are reported in Table III below, in which the following conventions were used:
(i) DC is the degree of conversion of the ketone in question;
(ii) YD is the yield of the product in question;

$$YD = \frac{\text{number of moles of product formed}}{\text{number of moles of initial substrate}} \times 100$$

(iii) Me represents a methyl radical;
(iv) Ph represents a phenyl radical;
(v) i-Pr represents an isopropyl radical; and
(vi) Q is the amount of catalyst charged.

TABLE III

| Example | SUBSTRATE TYPE | mmol | Q(mmol) | Time (h) | DC (%) | PRODUCT TYPE | YD (%) |
|---------|----------------|------|---------|----------|--------|--------------|--------|
| 16 | 2-methylcyclopentanone (=O, Me) | 4.4 | 0.025 | 2 | 96 | $CH_3-C(O)-(CH_2)_3-COOH$ | 94 |
| 17 | 2-phenylcyclohexanone (=O, Ph) | 2.4 | 0.015 | 6 | 96 | $Ph-C(O)-(CH_2)_4-COOH$ | 90 |
| 18 (*) | 2,4-dimethylcyclopentanone (Me, =O, Me) | 4.0 | 0.025 | 2 | 99 | $CH_3-C(O)-CH_2-CH(CH_3)-CH_2-COOH$ | 94 |
| 19 | 2,6-dimethylcyclohexanone (Me, =O, Me) | 11.0 | 0.075 | 6 | 91 | $CH_3-C(O)-(CH_2)_3-CH(CH_3)-COOH$ | 89 |

TABLE III-continued

| | SUBSTRATE | | | | | PRODUCT | |
|---|---|---|---|---|---|---|---|
| Example | TYPE | mmol | Q(mmol) | Time (h) | DC (%) | TYPE | YD (%) |
| 20 | i-Pr 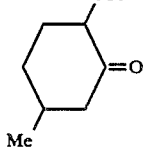 | 8.70 | 0.070 | 24 | 88 | i-Pr—C(O)—(CH$_2$)$_2$—CH(CH$_3$)—CH$_2$—COOH | 84 |

(*) 2 cm$^3$ acetonitrile

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aliphatic carboxylic acid, comprising oxidizing a monocyclic ketone with molecular oxygen or an oxygen-containing gas, in the presence of a catalytically effective amount of a vanadium compound having one of the following formulae (I) and (II):

$$H_{3+n}[PM_{12-n}V_nO_{40}]\cdot yH_2O \quad (I)$$

$$VO(Y)_m \quad (II)$$

in which n is an integer greater than or equal to 1 and less than or equal to 6; M is a molybdenum or tungsten atom; y is an integer ranging from zero to less than 50; Y is an acetylacetonate group or an alkoxy radical containing from 1 to 10 atoms; and m is 2 or 3.

2. The process as defined by claim 1, carried out in a liquid reaction medium.

3. The process as defined by claim 2, said liquid reaction medium comprising an inert solvent or diluent.

4. The process as defined by claim 3, said inert solvent or diluent comprising acetonitrile.

5. The process as defined by claim 1, said vanadium catalyst having the formula (I).

6. The process as defined by claim 5, wherein said vanadium catalyst having the formula (I), n is 1 or 2 and y is an integer ranging from 30 to 40.

7. The process as defined by claim 5, wherein said vanadium catalyst having the formula (I), M is a molybdenum atom.

8. The process as defined by claim 1, carried out at a temperature ranging from 25° to 120° C.

9. The process as defined by claim 1, carried out under a partial oxygen pressure ranging from 0.2 to 20 bar.

10. The process as defined by claim 1, wherein the concentration of vanadium in the reaction medium ranges from 0.001 to 0.5 mol.l$^{-1}$.

11. The process as defined by claim 1, wherein said monocyclic ketone comprises cyclohexanone.

12. The process as defined by claim 2, said reaction medium comprising an alcohol.

13. The process as defined by claim 8, carried out at a temperature of from 40° to 100° C.

14. The process as defined by claim 10, wherein the concentration of vanadium in the reaction medium ranges from 0.005 to 0.1 mol.l$^{-1}$.

15. The process as defined by claim 1, comprising the preparation of adipic acid.

* * * * *

REEXAMINATION CERTIFICATE (2983rd)

United States Patent [19]

Bregeault et al.

[11] B1 4,983,767

[45] Certificate Issued Sep. 3, 1996

[54] PREPARATION OF ALIPHATIC CARBOXYLIC ACIDS BY OXIDATION OF MONOCYCLIC KETONES

[75] Inventors: Jean-Marie Bregeault, Boussy Saint-Antoine; Bassam El-Ali, Paris Cedex; Jacques Martin, Orsay, all of France

[73] Assignee: Rhone-Poulenc Chimie, Courbevoie, France

Reexamination Request:
No. 90/003,268, Nov. 29, 1993

Reexamination Certificate for:
Patent No.: 4,983,767
Issued: Jan. 8, 1991
Appl. No.: 393,803
Filed: Aug. 15, 1989

[30] Foreign Application Priority Data

Aug. 16, 1988 [FR] France .................. 88 11075

[51] Int. Cl.⁶ .................................................. C07C 51/245
[52] U.S. Cl. .......................... 562/528; 502/152; 502/209; 502/312; 562/590
[58] Field of Search ........................... 562/528, 590; 502/152, 209, 312

[56] References Cited

U.S. PATENT DOCUMENTS

| | | | |
|---|---|---|---|
| 3,780,098 | 12/1973 | Morris | 562/528 |
| 3,855,307 | 12/1974 | Rony et al. | 562/406 X |
| 4,423,018 | 12/1983 | Lester et al. | 562/528 X |
| 4,510,321 | 4/1985 | Masilamani et al. | 562/421 |
| 4,739,114 | 4/1988 | Lee et al. | 562/524 |
| 4,883,910 | 11/1988 | Seidel | 562/528 |

*Primary Examiner*—Gary Geist

[57] ABSTRACT

Aliphatic carboxylic acids, e.g., adipic acid, are prepared by oxidizing a monocyclic ketone with molecular oxygen or an oxygen-containing gas, in the presence of a catalytically effective amount of a vanadium compound having one of following formulae (I) and (II):

$$H_{3+n}[PM_{12-n}V_nO_{40}] \cdot y\, H_2O \quad (I)$$

$$VO(Y)_m \quad (II)$$

in which n is an integer greater than or equal to 1 and less than or equal to 6; M is a molybdenum or tungsten atom; y is an integer ranging from zero to less than 50; Y is an acetylacetonate group or an alkoxy radical containing from 1 to 10 atoms; and m is 2 or 3.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 5 are cancelled.

Claims 2, 6–11 and 15 are determined to be patentable as amended.

Claims 3–4 and 12–14, dependent on an amended claim, are determined to be patentable.

New claims 16–29 are added and determined to be patentable.

2. The process as defined by claim [1] *16*, carried out in a liquid reaction medium.

6. The process as defined by claim [5] *16*, wherein [said vanadium catalyst having the formula (I),] n is 1 or 2 and y is an integer ranging from 30 to 40.

7. The process as defined by claim [5] *16*, wherein [said vanadium catalyst having the formula (I),] M is a molybdenum atom.

8. The process as defined by claim [1] *16*, carried out at a temperature ranging from 25° to 120° C.

9. The process as defined by claim [1] *16*, carried out under a partial oxygen pressure ranging from 0.2 to 20 bar.

10. The process as defined by claim [1] *16*, wherein the concentration of vanadium in the reaction medium ranges from 0.001 to 0.5 mol.l$^{-1}$.

11. The process as defined by claim [1] *16*, wherein said monocyclic ketone comprises cyclohexanone.

15. The process as defined by claim [1] *16*, comprising the preparation of adipic acid.

*16. A process for the preparation of an aliphatic carboxylic acid comprising oxidizing a monocyclic ketone with molecular oxygen or an oxygen-containing gas, in the presence of a catalytically effective amount of a vanadium compound having the following formula (I):*

$$H_{3+n}(PM_{12-n}V_nO_{40}) \cdot yH_2O \quad (I)$$

*in which n is an integer greater than or equal to 1 and less than or equal to 6; M is a molybdenum or tungsten atom; and y is an integer ranging from zero to less than 50.*

*17. A process for the preparation of an aliphatic carboxylic acid comprising oxidizing a monocyclic ketone with molecular oxygen or an oxygen-containing gas, in the presence of a catalytically effective amount of a vanadium compound having the following formula (II):*

$$VO(Y)_m \quad (II)$$

*in which Y is an alkoxy radical containing from 1 to 10 carbon atoms; and m is 2 or 3.*

*18. The process as defined by claim 17, carried out in a liquid reaction medium.*

*19. The process as defined by claim 18, said liquid reaction medium comprising an inert solvent or diluent.*

*20. The process as defined by claim 19, said inert solvent or diluent comprising acetonitrile.*

*21. The process as defined by claim 17, carried out at a temperature ranging from 25° to 120° C.*

*22. The process as defined by claim 17, carried out under a partial oxygen pressure ranging from 0.2 to 20 bar.*

*23. The process as defined by claim 17, wherein the concentration of vanadium in the reaction medium ranges from 0.001 to 0.5 mol.l$^{-1}$.*

*24. The process as defined by claim 17, wherein said monocyclic ketone comprises cyclohexanone.*

*25. The process as defined by claim 18, said reaction medium comprising an alcohol.*

*26. The process as defined by claim 21, carried out at a temperature of from 40° to 100° C.*

*27. The process as defined by claim 17, wherein the concentration of vanadium in the reaction medium ranges from 0.005 to 0.1 mol.l$^{-1}$.*

*28. The process as defined by claim 17, comprising the preparation of adipic acid.*

*29. A process for the preparation of an aliphatic carboxylic acid comprising oxidizing a monocyclic ketone with molecular oxygen or an oxygen-containing gas, in the presence of a catalytically effective amount of a vanadium compound having the following formula (II):*

$$VO(Y)_m \quad (II)$$

*in which Y is an isopropoxy radical; and m is 3.*

\* \* \* \* \*